(12) United States Patent
Diguet et al.

(10) Patent No.: US 8,597,642 B2
(45) Date of Patent: Dec. 3, 2013

(54) TABLETTABLE FORMULATIONS OF LIPOPHILIC HEALTH INGREDIENTS

(75) Inventors: Sylvain Diguet, Hagenthal-le-haut (FR); Bruno H. Leuenberger, Rheinfelden (CH); Bernd Schlegel, Rheinfelden (DE); Johann Ulm, Oberwil (CH)

(73) Assignee: DSM IP Assets B.V., Heerlen (NL)

( * ) Notice: Subject to any disclaimer, the term of this patent is extended or adjusted under 35 U.S.C. 154(b) by 640 days.

(21) Appl. No.: 12/669,057

(22) PCT Filed: Jul. 21, 2008

(86) PCT No.: PCT/EP2008/005945
§ 371 (c)(1), (2), (4) Date: Jun. 16, 2010

(87) PCT Pub. No.: WO2009/010305
PCT Pub. Date: Jan. 22, 2009

(65) Prior Publication Data
US 2010/0284987 A1    Nov. 11, 2010

Related U.S. Application Data

(60) Provisional application No. 60/929,945, filed on Jul. 19, 2007.

(51) Int. Cl.
*A61K 31/07* (2006.01)
(52) U.S. Cl.
USPC .................. 424/94.4; 424/400; 514/725
(58) Field of Classification Search
None
See application file for complete search history.

(56) References Cited

U.S. PATENT DOCUMENTS

| | | | |
|---|---|---|---|
| 5,935,826 | A | 8/1999 | Blue |
| 6,077,558 | A | 6/2000 | Euber |
| 7,868,172 | B2 | 1/2011 | Schiemann et al. |
| 2005/0118208 | A1* | 6/2005 | Bewert et al. .............. 424/401 |
| 2008/0026037 | A1 | 1/2008 | Christensen |
| 2011/0142928 | A1 | 6/2011 | Piene |

FOREIGN PATENT DOCUMENTS

| | | |
|---|---|---|
| EP | 0 972 513 | 1/2000 |
| EP | 1 935 410 | 6/2008 |
| JP | 6-172170 | 6/1994 |
| JP | 11-240901 | 9/1999 |
| JP | 2004-222649 | * 12/2004 |
| JP | 2004-222649 A | * 12/2004 |
| WO | WO 2006/081958 | 8/2006 |
| WO | WO 2007-003543 | 1/2007 |
| WO | WO 2007/009601 | 1/2007 |
| WO | WO 2007/045488 | 4/2007 |
| WO | WO 2007/090614 | 8/2007 |
| WO | WO2007/090614 | * 8/2007 |

OTHER PUBLICATIONS

Maywald et al., Agricultural and Food Chemistry, vol. 5(7), p. 528-531; published Jul. 1957.*
Hirose et al, "Agent for Preventing Color Fading of Colorant", English machine translation of JP2004-222649A, published Aug. 12, 2004.
International Search Report for PCT/EP2008/005945, mailed Jan. 22, 2009.
Anonymous: "Production of High Load Carotenoid Product Forms with Modified Food Starch", Research Disclosure, Mason Publications No. 452072, (Dec. 10, 2001), pp. 1-2.

* cited by examiner

*Primary Examiner* — Janet Epps-Smith
*Assistant Examiner* — Yanzhi Zhang
(74) *Attorney, Agent, or Firm* — Nixon & Vanderhye P.C.

(57) ABSTRACT

The present invention is directed to a formulation of a lipophilic health ingredient comprising a lipophilic health ingredient, a protective colloid comprising a modified starch and an emulsifier. The present invention is further directed to a formulation of (a) lipophilic health ingredient(s) comprising (a) lipophilic health ingredient(s) and a protective colloid, wherein said protective colloid is a modified starch, characterized in that the formulation has a residual moisture content ≤6.5 weight-%, based on the total weight of the formulation, as well as to a process for their manufacture. The latter formulations are especially suitable for the preparation of stable tablets of these lipophilic health ingredients.

30 Claims, No Drawings

TABLETTABLE FORMULATIONS OF LIPOPHILIC HEALTH INGREDIENTS

This application is the U.S. national phase of International Application No. PCT/EP2008/005945 filed 21 Jul. 2008, which designated the U.S. and claims the benefit of U.S. Provisional No. 60/929,945 filed 19 Jul. 2007, the entire contents of each of which are hereby incorporated by reference.

The present invention is directed to a formulation of a lipophilic health ingredient comprising a lipophilic health ingredient, a protective colloid comprising a modified starch and an emulsifier. The present invention is further directed to a formulation of (a) lipophilic health ingredient(s) comprising (a) lipophilic health ingredient(s) and a protective colloid, wherein said protective colloid is a modified starch, characterized in that the formulation has a residual moisture content ≤6.5 weight-%, based on the total weight of the formulation, as well as to a process for their manufacture. The latter formulations are especially suitable for the preparation of stable tablets of these lipophilic health ingredients.

Preferably the lipophilic health ingredient is Vitamin A or any derivative thereof or coenzyme Q10 or any derivative thereof; the derivatives being preferably esters, such as the acetates. More preferably are Vitamin A esters, most preferably is Vitamin A acetate and the corresponding formulation having a Vitamin A content of at least 1 weight-%, preferably of at least 5 weight-%, based on the total weight of the formulation.

DETAILED DESCRIPTION OF THE INVENTION

The present invention is directed to a formulation of a lipophilic health ingredient comprising a lipophilic health ingredient and a protective colloid, wherein said protective colloid is a modified starch, characterized in that the formulation has a residual moisture content ≤6.5 weight-%, preferably it has a residual moisture content ≤5 weight-%, more preferably it has a residual moisture content ≤4.5 weight-%, based on the total weight of the formulation.

Moisture Content of the Formulations According to the Present Invention

Preferably the formulations according to the present invention have a minimum residual moisture content ≥1 weight-%, more preferably they have a minimum residual moisture content ≥2 weight-%, based on the total weight of the formulation.

Even more preferred are formulations having a residual moisture content in the range of from 1 to 6.5 weight-%, in the range of from 2 to 6.5 weight-%, in the range of from 2 to 5 weight-%, most preferred are those formulations having a residual moisture content in the range of from 2.4 to 4.5 weight-%, based on the total weight of the formulation.

The residual moisture content is determined by the following procedure:
  providing 1 g of a formulation (sample) according to the present invention;
  drying the sample for 30 minutes at 105° C. in a halogen dryer HG 63P (Mettler, Switzerland);
  immediately after drying determining the actual weight of the sample (residual weight);
  calculating the weight loss in weight-%.

Alternatively a Karl-Fischer titration may be carried out to determine the residual moisture content.

Other Characteristics of the Formulations According to the Present Invention

In a further aspect of the invention the formulations as described above show additionally to the low moisture content an extrusion loss of said lipophilic health ingredient of ≤18%, preferably of ≤15%, more preferably of ≤12.5%, most preferably of ≤10% (i.e. an extrusion loss in the range of from 0 to 10%) when pressed to tablets, i.e. the amount of said lipophilic health ingredient present at the surface of tablets of these formulations is ≤18 weight-%, preferably ≤15 weight-%, more preferably ≤12.5 weight-%, most preferably ≤10 weight-%, based on the total weight of the lipophilic health ingredient in the formulation. Lipophilic health ingredients present at the surface of such a tablet is a great disadvantage since the lipophilic health ingredient is no longer protected against oxidation by the protective colloid. Extrusion losses in the range of from 5 to 12.5 weight-% are quite accepted for most purposes.

The extrusion loss is determined by
  cautious milling of the tablets to a mix so that the formulation itself is not destroyed by using a mortar;
  treating said mix with a suitable solvent (e.g. methylene chloride or petrolether) so that only the fat-soluble active ingredient which has been pressed out is dissolved;
  diluting the solution (solvent+fat-soluble active ingredient) with another solvent (cyclohexane or isopropanol) and
  analytical determination of the fat-soluble active ingredient in the solvent by measuring the absorption of the solution, and
  calculation of the percentage of the total amount of the fat-soluble active ingredient pressed out.

The extrusion loss is a relevant parameter for the shelf life of (pharmaceutical) tablets, i.e. a parameter for the stability of the fat-soluble active ingredient in the (pharmaceutical) tablets. If the extrusion loss is smaller, the shelf life of the tablets is longer.

Lipophilic Health Ingredient

The lipophilic health ingredient is in general any ingredient that has a beneficial effect for the health of a human and is not soluble or nearly not soluble in water at room temperature and at atmospheric pressure.

Preferably the lipophilic health ingredient is selected from the group consisting of fat-soluble vitamins (A, D, E, K, CoQ 10) or derivatives thereof (such as their acetates, e.g. vitamin A acetate or tocopherol acetate, or their longer chain fatty acid esters, e.g. vitamin A palmitate or tocopherol palmitate), carotenoids (especially α-carotene, β-carotene, 8'-apo-β-carotenal, 8'-apo-β-carotenoic acid esters such as the ethyl ester, canthaxanthin, astaxanthin, astaxanthin ester, lycopene, lutein, lutein (di) ester, zeaxanthin or crocetin, α- or β-zeacarotene or mixtures thereof), polyunsaturated fatty acids (PUFAs) or derivatives thereof, and triglycerides rich in polyunsaturated fatty acids such as eicosapentaenoic acid (EPA), docosahexaenoic acid (DHA) or γ-linolenic acid (GLA).

More preferably the lipophilic health ingredient is selected from the group consisting of the fat-soluble vitamins A, E, K, CoQ10 and their derivatives, the carotenoids β-carotene, lutein, lycopene, zeaxanthin and canthaxanthin, and polyunsaturated fatty acids and derivatives thereof.

Even more preferably the lipophilic health ingredient is Vitamin A or any derivative thereof or coenzyme Q10 or any derivative thereof; the derivatives being preferably esters, such as the acetates. Even more preferably are Vitamin A esters, most preferably is Vitamin A acetate and the corresponding formulation having a Vitamin A content of at least 1 weight-%, preferably of at least 5 weight-%, based on the total weight of the formulation. Such formulations usually have a Vitamin A activity in the range of from 250000 to 500000 International Units.

Preferably the amount of the lipophilic health ingredient in the formulations according to the present invention is in the range of from 1 to 50 weight-%, preferably in the range of from 5 to 20 weight-%, more preferably in the range of from 5 to 15 weight-%, based on the total weight of the formulation.

Protective Colloid

The protective colloids in the formulations of the present invention are modified starches or mixtures of modified starches with sugars such as sucrose. Preferably the weight ratio between the modified starch and the sugar varies in the range of from (100-10) to (0-90), more preferably it varies in the range of from 3 to (1-4).

In contrast to starches (non-modified starches) which are hydrophilic and therefore do not have emulsifying capacities, modified starches do have emulsifying capacities.

Modified starches are e.g. made from starches substituted by known chemical methods with hydrophobic moieties. For example starch may be treated with cyclic dicarboxylic acid anhydrides such as succinic anhydrides, substituted with a hydrocarbon chain (see O. B. Wurzburg (editor), "Modified Starches: Properties and Uses, CRC Press, Inc. Boca Raton, Fla., 1986 (and subsequent editions). A particularly preferred modified starch of this invention has the following formula (I)

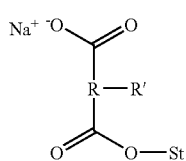

(I)

wherein St is a starch, R is an alkylene radical and R' is a hydrophobic group. Preferably R is a lower alkylene radical such as dimethylene or trimethylene. R' may be an alkyl or alkenyl group, preferably having 5 to 18 carbon atoms. A preferred compound of formula (I) is an "OSA-starch" (starch sodium octenyl succinate). The degree of substitution, i.e. the number of esterified hydroxyl groups to the number of free non-esterified hydroxyl groups usually varies in a range of from 0.1% to 10%, preferably in a range of from 0.5% to 4%, more preferably in a range of from 3% to 4%.

The term "OSA-starch" denotes any starch (from any natural source such as corn, waxy maize, waxy corn, wheat, tapioca and potato or synthesized) that was treated with octenyl succinic anhydride (OSA). The degree of substitution, i.e. the number of hydroxyl groups esterified with OSA to the number of free non-esterified hydroxyl groups usually varies in a range of from 0.1% to 10%, preferably in a range of from 0.5% to 4%, more preferably in a range of from 3% to 4%. OSA-starches are also known under the expression "modified food starch".

These OSA-starches may contain further hydrocolloids, such as starch, maltodextrin, carbohydrates, gum, corn syrup etc. and optionally any typical emulsifier (as co-emulsifier), such as mono- and diglycerides of fatty acids, polyglycerol esters of fatty acids, lecithins, sorbitan monostearate, and plant fibre or sugar.

The term "OSA-starches" encompasses also such starches that are commercially available e.g. from National Starch under the tradenames HiCap 100, Capsul, Capsul HS, Purity Gum 2000, UNI-PURE, HYLON VII; from Roquette Freres; from CereStar under the tradename C*EmCap or from Tate & Lyle.

It is also possible to use mixtures of modified starches, especially mixtures of OSA-starches. The weight-ratios of a mixture of two different OSA-starches may vary in a range of from 1:99 to 99:1. Preferably a mixture of HiCap 100 and Capsul HS is used. More preferably a mixture of 50 to 80 weight-% of HiCap 100 and 20 to 50 weight-% of Capsul HS is used. Most preferably a mixture of 50 weight-% of HiCap 100 and 50 weight-% of Capsul HS is used.

The terms "modified starches" and "OSA-starches" encompass further also modified starches/OSA-starches that were partly hydrolysed enzymatically, e.g. by glycosylases (EC 3.2; see http://www.chem.qmul.ac.uldiubmb/enzyme/EC3.2/) or hydrolases, as well as to modified starches/OSA-starches that were partly hydrolysed chemically by know methods. The terms "modified starches" and "OSA-starches" encompass also modified starches/OSA-starches that were first partly hydrolysed enzymatically and afterwards additionally hydrolysed chemically. Alternatively it may also be possible to first hydrolyse starch (either enzymatically or chemically or both) and then to treat this partly hydrolysed starch with cyclic dicarboxylic acid anhydrides such as succinic anhydrides, substituted with a hydrocarbon chain, preferably to treat it with octenyl succinic anhydride.

The enzymatical hydrolysis is conventionally carried out at a temperature of from about 5 to about <100° C., preferably at a temperature of from about 5 to about 70° C., more preferably at a temperature of from about 20 to about 55° C.

The glycosylases/hydrolases can be from fruit, animal origin, bacteria or fungi. The glycolase/hydrolase may have endo-activity and/or exo-activity. Therefore, enzyme preparations of endo- and exo-glycosylases/-hydrolases or any of their mixtures may be used. Usually the glycosylases/hydrolases show also unknown side activities, but which are not critical for the manufacture of the desired product.

Examples of glycosylases are the commercially available enzyme preparations from the suppliers Novozymes, Genencor, AB-Enzymes, DSM Food Specialities, Amano, etc.

Preferably the hydrolases are α-amylases, glucoamylases, β-amylases or debranching enzymes such as isoamylases and pullulanases.

The glycosylase/hydrolase is added to provide a concentration of from about 0.01 to about 10 weight-%, preferably of from about 0.1 to about 1 weight-%, based on the dry weight of the modified starch/OSA-starch. Preferably the enzyme is added at once. The enzymatic hydrolysis may also be carried out stepwise. For instance, the glycosylase/hydrolase or a mixture of glycosylases/hydrolases is added to the incubation batch in an amount of e.g. 1% whereupon, e.g. after 5 to 10 minutes (at a temperature of 35° C.) further glycosylase/hydrolase or a mixture of glycosylases/hydrolases which may by the same or different from the first added glycosylase/hydrolase or mixture of glycosylases/hydrolases is added, e.g. in an amount of 2% whereupon the incubation batch is hydrolysed at 35° C. for 10 minutes. Using this procedure, starting modified starches/OSA-starches having a degree of hydrolysis of approximately zero can be used.

The duration of hydrolysis may vary between about a few seconds and about 300 minutes. The exact duration of the enzymatic treatment may be determined in an empirical way with respect to the desired properties of the modified starch/OSA-starch, such as emulsifying stability, emulsifying capacity, droplet size of the emulsion, depending strongly on parameters like enzyme activities, or composition of the substrate. Alternatively it may be determined by measuring the osmolality (W. Dzwokak and S. Ziajka, Journal of food science, 1999, 64 (3) 393-395).

The inactivation of the glycosylase/hydrolase is suitably achieved by heat denaturation, e.g. by heating of the incubation batch to about 80 to 85° C. for 5 to 30 minutes, especially for 5 to 10 minutes.

Preferably the amount of the protective colloid in the formulations according to the present invention is in the range of from 50 to 99 weight-%, preferably in the range of from 80 to 95 weight-%, more preferably in the range of from 85 to 95 weight-%, based on the total weight of the formulation.

If further ingredients (see below) such as fat-soluble excipient(s) and/or adjuvant(s), water-soluble excipient(s) and/or adjuvant(s), antioxidants (preferably present in an amount of from 1-5 weight-%, based on the total weight of the formulation), emulsifiers (preferably present in an amount of from 0-10 weight-%, based on the total weight of the formulation) or in case of beadlets (manufactured by a powder-catch process) coatings of e.g. corn starch (present in an amount of from 0-40 weight-%, preferably in an amount of from 0-25 weight-%, based on the total weight of the formulation) are present, the amount of the protective colloid may be correspondingly lower.

Further Optional/Preferred Components of the Formulations of the Present Invention The formulations according to the present invention may further contain one or more water-soluble excipient(s) and/or adjuvant(s), one or more fat-soluble excipient(s) and/or adjuvant(s), one or more antioxidant(s) and/or one or more emulsifier(s).

Water-Soluble Excipients and/or Adjuvants

Examples of water-soluble excipients and/or adjuvants are monosaccharides, disaccharides, oligosaccharides and polysaccharides, glycerol and water-soluble antioxidants.

Antioxidants

The antioxidants may be water-soluble or fat-soluble. Preferably they are antioxidants that are suitable for the human consumption, i.e. so-called "food antioxidants"-antioxidants suitable for food.

More preferably the antioxidant is selected from the group consisting of tocopherols, mixed tocopherols, vitamin E, sodium ascorbate, 2,6-ditertbutyl-4-methylphenol (BHT) and 2-tert-butyl-4-hydroxyanisol (BHA), propyl gallate, rosemary extract, nordihydroguiaretic acid and mixtures thereof.

Even more preferably the antioxidant is selected from the group consisting of (mixed) tocopherols, BHT, BHA and mixtures thereof.

Most preferably the antioxidant is selected from the group consisting of tocopherol, BHT and BHA.

Preferably the amount of the antioxidant in the formulations according to the present invention is in the range of from 1 to 5 weight-%, based on the total weight of the formulation.

Emulsifiers

Furthermore, the formulation according to the present invention may further contain an emulsifier.

Preferably the emulsifier is selected from the group consisting of polyoxyethylen(x) sorbitan mono-$C_{10}$-$C_{20}$-alkan (dien/trien/pentaen) oates with x being an integer in the range of from 4 to 20 (preferably with x being 4, 5 or 20), polyoxyethylene(x) sorbitan tri-$C_{10}$-$C_{20}$-alkan(dien/trien/pentaen) oates with x being an integer in the range of from 4 to 20 (preferably with x being 4, 5 or 20), sugar esters, fatty acid esters, ascorbyl palmitate and mixtures thereof.

More preferably the emulsifier is selected from the group consisting of polyoxyethylene(20) sorbitan mono-laurate, polyoxyethylene(4) sorbitan mono-laurate, polyoxyethylene (20) sorbitan mono-palmitate, polyoxyethylene(20) sorbitan mono-stearate, polyoxyethylene(4) sorbitan mono-stearate, polyoxyethylene(20) sorbitan tri-stearate, polyoxyethylene (20) sorbitan mono-oleate, polyoxyethylene(5) sorbitan mono-oleate, polyoxyethylene(20) sorbitan tri-oleate and mixtures thereof. These emulsifiers are e.g. commercially available from Uniqema under the trade names Tween® 20, Tween® 21, Tween® 40, Tween® 60, Tween® 61, Tween® 65, Tween® 80, Tween® 81 and Tween® 85.

Most preferably the emulsifier is polyoxyethylene(20) sorbitan monostearate (Tween® 60).

Preferably the amount of the emulsifier (with the preferences as given above) in the formulations according to the present invention is in the range of from 0 to 10 weight-%, based on the total weight of the formulation.

Most Preferred Embodiments of the Present Invention

One of the most preferred formulations of the present invention contains

| Compound | Amount | Preferred amount | More preferred amount |
|---|---|---|---|
| Vitamin A acetate | 5 to 15 weight-% | 10 to 15 weight-% | 11 to 12 weight-% |
| DL-alpha-tocopherol (or any other stabilizer) | 1 to 5 weight-% | 1 to 2 weight-% | — |
| modified food starch (especially OSA-starch) | 30 to 50 weight-% | 35 to 45 weight-% | 38 to 42 weight-% |
| sucrose | 20 to 35 weight-% | 20 to 30 weight-% | 25 to 30 weight-%; most preferred: 25 to 29 weight-% |
| a coating of corn starch | 5 to 40 weight-% | 15 to 25 weight-% | 18 to 22 weight-% | each amount based on the total weight of the formulation; and has a residual moisture content of ≤6.5 weight-%, based on the total weight of the formulation. Further ingredients as named above may also be present.

The other most preferred formulations of the present invention contains

| Compound | Amount | Preferred amount | More preferred amount |
|---|---|---|---|
| Coenzyme Q10 | 5 to 15 weight-% | 8 to 12 weight-% | — |
| medium chain triglycerides | 1 to 10 weight-% | 2 to 8 weight-% | 3 to 5 weight-% |
| modified food starch (especially OSA-starch) | 40 to 60 weight-% | 45 to 60 weight-% | 50 to 55 weight-% |
| sucrose | 10 to 25 weight-% | 12 to 20 weight-% | 15 to 20 weight-% |
| a coating of corn starch | 10 to 25 weight-% | 12 to 20 weight-% | 15 to 20 weight-% | each amount based on the total weight of the formulation; and has a residual moisture content of ≤6.5 weight-%, based on the total weight of the formulation. Further ingredients as named above may also be present.

Tablets According to the Present Invention

The formulations according to the present invention are especially suitable for the manufacture of tablets of these lipophilic health ingredients with the preferences as given above.

Thus, the present invention is also directed to tablets comprising a formulation according to the present invention. The tablets may be any pharmaceutical that preferably contains Vitamin A or a derivative thereof, especially any pharmaceutical that contains Vitamin A acetate.

Preferably those tablets are multivitamin tablets and tablets comprising mineral salts and/or trace elements, as well as multivitamin tablets also containing mineral salts and/or trace elements.

Those multivitamin tablets may contain vitamin E, vitamin C, vitamin K, vitamin B1, vitamin B2, vitamin B6, vitamin B12, vitamin D, biotin, folic acid, niacin, niacin amide, pantothenic acid and/or pantothenate. Instead of these compounds also the corresponding derivatives and salts may be used.

Those mineral salts-tablets may contain calcium, phosphor, magnesium, potassium, iron, manganese, selenium, copper, chloride, molybdenum, chrome, zinc and/or iodine salts.

Especially preferred is the use of a formulation according to the present invention of Vitamin A for the manufacture of a tablet comprising other water- and fat-soluble vitamins such as vitamin E, vitamin C, vitamin K, vitamin B1, vitamin B2, vitamin B6, vitamin B 12, vitamin D and their derivatives or salts.

Process for the Manufacture of a Formulation According to the Present Invention

The process for the manufacture of a formulation of a lipophilic health ingredient, wherein said formulation has a residual moisture content ≤6.5 weight-%, based on the total weight of the formulation, comprises the following steps:

a) preparing an aqueous solution or colloidal solution of a modified starch;

b) optionally adding at least a water-soluble excipient and/or adjuvant to the solution prepared in step a);

c) preparing a solution or dispersion of at least a lipophilic health ingredient, and optionally at least a fat-soluble adjuvant and/or excipient;

d) mixing the solutions prepared in step a) (or b)) and c) with each other;

e) homogenising the thus resulting mixture;

f) converting the nano-emulsion/dispersion obtained in step e) into a powder, preferably into a beadlet;

g) drying said powder obtained in step f) to achieve a residual moisture content ≤6.5 weight-%, based on the total weight of the formulation.

Steps a) to f) of this process for the manufacture of the compositions of the present invention can be carried out in an according manner as disclosed for the preparation of matrix-based compositions of (fat-soluble) active ingredient and/or colorant compositions for enrichment, fortification and/or coloration of food, beverages, animal feed, cosmetics or pharmaceutical compositions, e.g. in EP-A 0 285 682, EP-A 0 347 751, EP-A 0 966 889, EP-A 1 066 761, EP-A 1 106 174, WO 98/15195, EP-A 0 937 412, EP-A 0 065 193 or the corresponding U.S. Pat. No. 4,522,743, WO 02/102298, EP-A 1 300 394 and in EP-A 0 347 751, the contents of which are incorporated herein by reference.

This process may be performed at industrial scale, i.e. at a scale to obtain several 100 kg to several tons of product. If the process in the plant is carried out continuously several 100 tons of product may be obtained.

Details of this process are discussed in the following.

Step a)

In step a) preferably an aqueous solution or suspension of a modified starch (with the definition and the preferences as described above) having a dry mass content in the range of from 0.1 to 80 weight-%, preferably in the range of from 0.5 to 80 weight-%, is prepared.

It is also possible to use mixtures of modified starches, especially mixtures of OSA-starches. The weight-ratios of a mixture of two different OSA-starches may vary in a range of from 1:99 to 99:1. Preferably a mixture of HiCap 100 and Capsul HS is used. More preferably a mixture of 50 to 80 weight-% of HiCap 100 and 20 to 50 weight-% of Capsul HS is used. Most preferably a mixture of 50 weight-% of HiCap 100 and 50 weight-% of Capsul HS is used.

Step a) is preferably carried out at a temperature in the range of from 20 to 80° C. and at atmospheric pressure.

During step a) other water-soluble ingredients of the final composition such as water-soluble antioxidants may also be added.

Step b)

Step b) is preferably carried out at the same temperature and at the same pressure as step a).

Step c)

The lipophilic health ingredient and optional fat-soluble excipients and adjuvents (e.g. emulsifiers and stabilizers) are either used as such or dissolved or suspended in an oil and/or an (organic) solvent. Most preferably the lipophilic health ingredient and optionally the fat-soluble excipients and adjuvents is/are dissolved or suspended in oil such as corn oil and/or triglycerides, especially in corn oil and/or middle chain triglycerides (MCT).

Suitable organic solvents are halogenated aliphatic hydrocarbons, aliphatic ethers, aliphatic and cyclic carbonates, aliphatic esters and cyclic esters (lactones), aliphatic and cyclic ketones, aliphatic alcohols and mixtures thereof.

Examples of halogenated aliphatic hydrocarbons are mono- or polyhalogenated linear, branched or cyclic $C_1$- to $C_{15}$-alkanes. Especially preferred examples are mono- or polychlorinated or -brominated linear, branched or cyclic $C_1$- to $C_{15}$-alkanes. More preferred are mono- or polychlorinated linear, branched or cyclic $C_1$- to $C_{15}$-alkanes. Most preferred are methylene chloride and chloroform.

Examples of aliphatic esters and cyclic esters (lactones) are ethyl acetate, isopropyl acetate and n-butyl acetate; and γ-butyrolactone.

Examples of aliphatic and cyclic ketones are acetone, diethyl ketone and isobutyl methyl ketone; and cyclopentanone and isophorone.

Examples of cyclic carbonates are especially ethylene carbonate and propylene carbonate and mixtures thereof.

Examples of aliphatic ethers are dialkyl ethers, where the alkyl moiety has 1 to 4 carbon atoms. One preferred example is dimethyl ether.

Examples of aliphatic alcohols are ethanol, iso-propanol, propanol and butanol.

Furthermore any oil (triglycerides), orange oil, limonen or the like and water can be used as a solvent.

Step b) is preferably carried out at the same temperature and at the same pressure as step a) and/or step b).

Step d)

Usually the lipophilic health ingredient or the solution or dispersion thereof, respectively, is then added to the aqueous (colloidal) solution of the modified starch with stirring.

Step e)

For the homogenisation conventional technologies, such as high-pressure homogenisation, high shear emulsification (rotor-stator systems), micronisation, wet milling, microchannel emulsification, membrane emulsification or ultrasonification can be applied. Other techniques are e.g. disclosed in EP-A 0 937 412 (especially paragraphs [0008], [0014], [0015], [0022] to [0028]), EP-A 1 008 380 (especially paragraphs [0005], [0007], [0008], [0012], [0022], [0023] to [0039]) and in U.S. Pat. No. 6,093,348 (especially column 2, line 24 to column 3, line 32; column 3, line 48 to 65; column 4, line 53 to column 6, line 60), the contents of which are incorporated herein by reference.

Step f)

The so-obtained nano-emulsion/dispersion, which is an oil-in-water dispersion, can be converted after removal of the organic solvent (if present) into a solid composition, e.g. a dry powder, using any conventional technology such as spray drying, spray drying in combination with fluidised bed granulation (the latter technique commonly known as fluidised spray drying or FSD), or by a powder-catch technique (resulting in the formation of beadlets) whereby sprayed emulsion droplets are caught in a bed of an absorbent, such as starch, and subsequently dried.

Step g)

The drying may be performed by any method know to the person skilled in the art to achieve the desired residual moisture content.

Preferably the drying according to step g) is carried out in a fluidized bed. This is also the preferred drying mode if the process is an industrial process.

If the process is carried out in the batch mode, the drying is preferably carried out at a temperature in the range of from 30-70° C., preferably at a temperature in the range of from 35-65° C., even more preferably at a temperature in the range of from 38-64° C., most preferably at a temperature in the range of from 50-60° C. The drying at these temperature ranges may last between 20-90 minutes, preferably between 30-70 minutes, more preferably between 30-45 minutes.

In a continuously carried out process step g) is more preferably carried out by drying the powder continuously in a fluidized bed with 4 different temperature zones. The total residence time in the fluidized bed may be from 1 to 5 hours.

Even more preferably said 4 different temperature zones have the following temperatures:

| Zone | Temperature | Preferred temperature | More preferred temperature |
|---|---|---|---|
| 1 | 20-50° C. | 25-45° C. | — |
| 2 | 30-70° C. | 35-65° C. | 38-64° C. |
| 3 | 45-65° C. | 48-62° C. | — |
| 4 | 45-80° C. | 45-75° C. | 50-73° C. |

Further Embodiment of the Present Invention

The present invention is also directed to a formulation of a lipophilic health ingredient comprising a lipophilic health ingredient, a protective colloid comprising a modified starch and an emulsifier—independent from the residual moisture content and the extrusion loss.

Examples and preferences of the lipophilic health ingredient are already given above.

The protective colloid may be modified starch (as described above incl. the preferences) or a mixture of a modified starch and sugar (also as described above incl. the preferences).

The emulsifier is preferably selected from the group consisting of polyoxyethylen(x) sorbitan mono-$C_{10}$-$C_{20}$-alkan (dien/trien/pentaen) oates with x being an integer in the range of from 4 to 20 (preferably with x being 4, 5 or 20), polyoxyethylene(x) sorbitan tri-$C_{10}$-$C_{20}$-alkan(dien/trien/pentaen) oates with x being an integer in the range of from 4 to 20 (preferably with x being 4, 5 or 20), sugar esters, fatty acid esters, ascorbyl palmitate and mixtures thereof.

More preferably the emulsifier is selected from the group consisting of polyoxyethylene(20) sorbitan mono-laurate, polyoxyethylene(4) sorbitan mono-laurate, polyoxyethylene(20) sorbitan mono-palmitate, polyoxyethylene(20) sorbitan mono-stearate, polyoxyethylene(4) sorbitan mono-stearate, polyoxyethylene(20) sorbitan tri-stearate, polyoxyethylene(20) sorbitan mono-oleate, polyoxyethylene(5) sorbitan mono-oleate, polyoxyethylene(20) sorbitan tri-oleate and mixtures thereof.

Most preferably the emulsifier is polyoxyethylene(20) sorbitan monostearate.

The amounts of the single components is as already disclosed above.

Preferably such formulations also have a residual moisture content and/or an extrusion loss as disclosed above.

The present invention is now illustrated in the following non-limiting examples.

EXAMPLES

The following abbreviations were used:
BHT=3,5-ditertbutyl-4-hydroxy toluene
BHA=2-butyl-4-hydroxy anisol
rpm=revolutions per minute

Example 1A-D 86.3 g of modified food starch (Capsul HS from National Starch), 57.0 g of glucose syrup (Glucidex IT 47 from Roquette) and 2.0 g of sodium ascorbate were placed in a 500 ml double wall vessel, 80 g of de-ionized water were added and the mixture was brought into solution while stirring with a mixer disc at 800 rpm and approximately 45° C., this solution is called matrix solution. Thereupon, 23.2 g of an oil mixture (20.3 g vitamin A acetate ($2.8 \times 10^6$ IE/g) and 2.9 g BHT melted at approximately 65° C.) were emulsified in this matrix and stirred for 15 minutes. During the emulsification and stirring the mixer disc was operated at 4800 rpm. After this emulsification the internal phase of the emulsion had an average particle size of about 137 nm (measured by laser diffraction). The emulsion was diluted with 40 g of de-ionized water and the temperature was held at 65° C.

Subsequently 1300 g of corn starch (fluidized with silicic acid) were placed in a laboratory spray pan and cooled to at least 0° C. The emulsion was sprayed into the spray pan using a rotating spray nozzle. The thus-obtained particles coated with corn starch were sieved off (sieve fraction 0.125 to 0.63 mm) from the excess corn starch and dried at room temperature using a stream of air. There were obtained 183 g of particles coated with corn starch which had outstanding flow properties, were completely dry and could be handled very well.

The trial was repeated four times. The collected dry powder was blended and splitted in four parts for additional drying using a lab fluid bed dryer (Retsch): part 1 without (example 1A), part 2 for 10 minutes at 40° C. and 10 minutes at 50° C. (example 1B), part 3 for 30 minutes at 60° C. (example 1C) and part four for 70 minutes at 60° C. (example 1D). The analytical data (residual moisture content and extrusion loss in tablets) as well as stability data are summarized in table 1.

The lower residual moisture content results beside the stability improvement also in a significant lower extrusion loss during tabletting. The extrusion loss is defined as the percentage of the active material which is extractable by an organic solvent out of the formulation, after being tabletted under defined conditions. Important: The matrix of the product form must not be soluble in the organic solvent. As known, the extrusion loss correlates with the stability in tablets.

Example 2A-C

In each case 200 g of the actual sales form All-QTM (Coenzyme Q10) 10% CWS/S (DSM Nutritional Products AG, Kaiseraugst, Switzerland) have been used for additional drying using a lab fluid bad dryer (Retsch):
a) without additional drying (example 2A)
b) additional drying for 30 minutes at 50° C. (example 2B)
c) additional drying for 45 minutes at 60° C. (example 2C)

The analytical data (residual moisture content and extrusion loss in tablets) are given in table 2.

TABLE 2

All-QTM (Coenzyme Q10) 10% CWS/S: Influence of residual moisture content on extrusion loss in tablets

| process conditions - measured parameters | Example | | |
|---|---|---|---|
| | Example 2A | Example 2B | Example 2C |
| Additional drying conditions | Without additional drying | 30 minutes at 50° C. | 45 minutes at 60° C. |
| Residual moisture content | 4.7% | 3.9% | 2.5% |
| Extrusion loss in tablets | 17.0% | 11.0% | 8.8% |

Example 3A-D

In each case a certain amount of the actual sales form Vitamin A Acetate 325 CWS/S (DSM Nutritional Products AG, Kaiseraugst, Switzerland) have been used for additional drying using a lab fluid bad dryer (Retsch):
a) without additional drying (example 3A)
b) additional drying for 10 minutes at 30° C. (example 3B)
c) additional drying for 45 minutes at 60° C. (example 3C)
c) additional drying for 45 minutes at 60° C. (example 3D)

TABLE 1

Vitamin A Acetate 250 CWS/S (lab trials): per se stability data
Storage conditions: product in sealed aluminum bags at 40° C. and at 75% relative humidity

| process conditions - measured parameters | Example | | | |
|---|---|---|---|---|
| | Example 1A | Example 1B | Example 1C | Example 1D |
| Additional drying conditions | Without additional drying | 10 minutes at 40° C. + 10 minutes at 50° C. | 30 minutes at 60° C. | 70 minutes at 60° C. |
| Residual moisture content | 5.9% | 4.8% | 3.6% | 2.9% |
| Extrusion loss in tablets | 10.9% | 8.9% | 6.7% | 5.7% |
| Vitamin A Acetate Retention (HPLC) | | | | |
| Initial | 100.0 | 100.0 | 100.0 | 100.0 |
| 1 month | 89.4 | 90.7 | 91.7 | 92.5 |
| 2 months | 78.2 | 81.7 | 85.7 | 87.3 |
| 3 months | 70.5 | 76.8 | 79.7 | 81.8 |
| 6 months | 51.8 | 62.0 | 66.5 | 69.6 |

The analytical data (residual moisture content and extrusion loss in tablets) are given in table 3.

TABLE 3

Vitamin A Acetate 325 CWS/S (ScaleUp): per se stability data
Storage conditions: product in sealed aluminum bags at 40° C.
and at 75% relative humidity

| process conditions - measured parameters | Example 3A | Example 3B | Example 3C | Example 3D |
|---|---|---|---|---|
| Additional drying conditions | Without | 10 minutes at 30° C. | 30 minutes at 50° C. | 30 minutes at 60° C. |
| Residual moisture content | 6.1% | 5.4% | 4.2% | 3.2% |
| Vitamin A Acetate Retention (HPLC) | | | | |
| Initial | 100.0 | 100.0 | 100.0 | 100.0 |
| 1 month | 79.5 | 83.9 | 89.6 | 92.5 |
| 2 months | 68.6 | 76.7 | 80.6 | 84.3 |
| 3 months | 59.2 | 64.6 | 71.2 | 76.3 |
| 6 months | 41.3 | 47.6 | 55.0 | 60.4 |
| 12 months | 19.8 | 26.3 | 34.0 | 39.3 |

The available stability data confirm the influence of the residual moisture on vitamin A stability.

Example 4A-D

In each case a certain amount of the actual sales form Vitamin A Acetate 325 CWS/S (DSM Nutritional Products AG, Kaiseraugst, Switzerland) have been used for additional drying using a lab fluid bad dryer (Retsch) with 4 zones:
a) additional drying at 25° C. (zone 1), at 38-52° C. (zone 2), at 48-60° C. (zone 3) and at 50-65° C. (zone 4) (example 4A);
b) additional drying at 25° C. (zone 1), at 38-52° C. (zone 2), at 48-60° C. (zone 3) and at 50-65° C. (zone 4) (example 4B);
c) additional drying at 35° C. (zone 1), at 63-64° C. (zone 2), at 62° C. (zone 3) and at 70-73° C. (zone 4) (example 4C);
d) additional drying at 45° C. (zone 1), at 63-64° C. (zone 2), at 62° C. (zone 3) and at 70-73° C. (zone 4) (example 4D).

The analytical data (residual moisture content and extrusion loss in tablets) are given in table 4.

TABLE 4

Vitamin A Acetate 325 CWS/S (industrial scale): per se stability data
Storage conditions: product in sealed aluminum bags at 40° C.
and at 75% relative humidity

| process conditions - measured parameters | Example 4A | Example 4B | Example 4C | Example 4D |
|---|---|---|---|---|
| Additional drying conditions | 25° C. 38-52° C. 48-60° C. 50-65° C. | 25° C. 38-52° C. 48-60° C. 50-65° C. | 35° C. 63-64° C. 62° C. 70-73° C. | 45° C. 63-64° C. 62° C. 70-73° C. |
| Residual moisture content | 4.6% | 4.0% | 2.8% | 3.3% |
| Extrusion loss in tablets | 15.7% | 15.6% | 12.2% | 14.3% |
| Vitamin A Acetate Retention (HPLC) | | | | |
| Initial | 100.0 | 100.0 | 100.0 | 100.0 |
| 1 month | 85.9 | 86.0 | 88.5 | 87.4 |
| 2 months | 79.0 | 80.1 | 82.3 | 82.7 |
| 3 months | 71.6 | 73.4 | 77.7 | 76.7 |

The stability results of the production lots confirm the stability improvement by reducing the residual moisture content in the final product.

The stability of samples/formulations prepared according to example 4A and 4D in multivitamin/multimineral tablets (containing Vitamin A, Vitamin D3, Vitamin C, biotin, folic acid, Vitamin B1, Vitamin B2, niacin amide, Vitamin B6, Vitamin B12, pantothenic acid, vitamin K1, and salts of the following minerals: iron, copper, manganese, zinc, iodine, chrome, selenium, molybdenum, potassium, calcium, phosphor) was tested. The test was performed at 40° C. and 75% relative humidity and led to the following results:

| Vitamin A Acetate Retention (HPLC) | Sample - Example 4A | Sample - Example 4D |
|---|---|---|
| Initial | 100% | 100% |
| 1 month | 85% | 94% |
| 2 months | 52% | 60% |

Example 5

82.8 g of modified food starch (Capsul HS from National Starch), 54.6 g of sugar and 2.9 g of polyoxyethylene sorbitan monostearate (Tween 60 from Uniqema) Company were placed in a 500 ml double wall vessel, 80 g of de-ionized water were added and the mixture was brought into solution while stirring with a mixer disc at 800 rpm and approximately 45° C., this solution is called matrix solution. Thereupon, 26.3 g of an oil mixture (23.0 g of vitamin A acetate ($2.8 \times 10^6$ IE/g) and 3.3 g BHT melted at approximately 65° C.) were emulsified in this matrix and stirred for 15 minutes. During the emulsification and stirring the mixer disc was operated at 4800 rpm. After this emulsification the internal phase of the emulsion had an average particle size of about 567 nm (measured by laser diffraction). The emulsion was diluted with 40 g of de-ionized water and the temperature was held at 65° C.

The dry powder was prepared as described in example 1.

272 g of particles coated with corn starch were obtained which had outstanding flow properties, were completely dry and could be handled very well.

The invention claimed is:

1. A formulation of a lipophilic health ingredient comprising ingredients selected from vitamin A, coenzyme Q10 and their esters and a protective colloid, wherein said protective colloid is a sodium octenyl succinate (OSA) starch, characterized in that the formulation has a residual moisture content ≤6.5 weight-%, based on the total weight of the formulation.

2. The formulation according to claim 1, wherein the formulation has a residual moisture content ≥1 weight-% to ≤6.5 weight-%, based on the total weight of the formulation.

3. The formulation according to claim 1, wherein the formulation has a residual moisture content in the range of from 2 to 5 weight-%, based on the total weight of the formulation.

4. The formulation according to claim 1, wherein the formulation shows an extrusion loss of said lipophilic health ingredient of ≤18 weight-%, based on the total weight of the lipophilic health ingredient in the formulation, when pressed to tablets.

5. The formulation according to claim 4, wherein the formulation shows an extrusion loss of said lipophilic health ingredient of ≤15 weight-% based on the total weight of the lipophilic health ingredient in the formulation, when pressed to tablets.

6. The formulation according to claim 1, wherein the formulation further contains an antioxidant.

7. The formulation according to claim 6, wherein the antioxidant is selected from the group consisting of tocopherols, mixed tocopherols, sodium ascorbate, 2,6-ditertbutyl-4-methylphenol (BHT) and 2-tert-butyl-4-hydroxyanisol (BHA), propyl gallate, rosemary extract, nordihydroguiaretic acid and mixtures thereof.

8. The formulation according to claim 7, wherein the antioxidant is selected from the group consisting of (mixed) tocopherols, BHT, BHA and mixtures thereof.

9. The formulation according to claim 1, wherein the formulation further contains an emulsifier.

10. The formulation according to claim 9, wherein the emulsifier is selected from the group consisting of polyoxyethylen(x) sorbitan mono-$C_{10}$-$C_{20}$-alkan(dien/trien/pentaen)oates with x being an integer in the range of from 4 to 20, polyoxyethylene(x) sorbitan tri-$C_{10}$-$C_{20}$-alkan(dien/trien/pentaen)oates with x being an integer in the range of from 4 to 20, sugar esters, fatty acid esters, ascorbyl palmitate and mixtures thereof.

11. The formulation according to claim 9, wherein the emulsifier is selected from the group consisting of polyoxyethylene(20) sorbitan mono-laurate, polyoxyethylene(4) sorbitan mono-laurate, polyoxyethylene(20) sorbitan mono-palmitate, polyoxyethylene(20) sorbitan mono-stearate, polyoxyethylene(4) sorbitan mono-stearate, polyoxyethylene(20) sorbitan tri-stearate, polyoxyethylene(20) sorbitan mono-oleate, polyoxyethylene(5) sorbitan mono-oleate, polyoxyethylene(20) sorbitan tri-oleate and mixtures thereof.

12. The formulation according to claim 9, wherein the emulsifier is polyoxyethylene(20) sorbitan monostearate.

13. A tablet comprising a formulation according to claim 1.

14. The tablet according to claim 13, wherein the tablet is a multivitamin tablet.

15. The tablet according to claim 13 further comprising mineral salts.

16. A process for the manufacture of a formulation of a lipophilic health ingredient selected from vitamin A, coenzyme Q10 and their esters, wherein said formulation has a residual moisture content ≤6.5 weight-%, based on the total weight of the formulation, comprising the following steps:
 a) preparing an aqueous solution or colloidal solution of an OSA starch;
 b) optionally adding at least a water-soluble excipient and/or adjuvant to the solution prepared in step a);
 c) preparing a solution or dispersion of at least a lipophilic health ingredient, and optionally at least a fat-soluble adjuvant and/or excipient;
 d) mixing the solutions prepared in step a) (or b)) and c) with each other;
 e) homogenising the thus resulting mixture;
 f) converting the nano-emulsion/dispersion obtained in step e) into a powder, preferably into a beadlet;
 g) drying said powder obtained in step f) to achieve a residual moisture content ≤6.5 weight-%, based on the total weight of the formulation.

17. The process according to claim 16, wherein the process is an industrial process.

18. The process according to claim 16, wherein step g) is carried out in a fluidized bed.

19. The process according to claim 17, wherein step g) is carried out by drying the powder continuously in a fluidized bed with 4 different temperature zones.

20. The process according to claim 19, wherein said 4 different temperature zones have the following temperatures: zone 1—temperature in the range of from 20-50° C.; zone 2—temperature in the range of from 30-70° C.; zone 3—temperature in the range of from 45-65° C.; and zone 4—temperature in the range of from 45-80° C.

21. A formulation of a lipophilic health ingredient comprising a lipophilic health ingredient and an emulsifier.

22. The formulation according to claim 21, wherein the emulsifier is selected from the group consisting of polyoxyethylen(x) sorbitan mono-$C_{10}$-$C_{20}$-alkan(dien/trien/pentaen)oates with x being an integer in the range of from 4 to 20, polyoxyethylene(x) sorbitan tri-$C_{10}$-$C_{20}$-alkan(dien/trien/pentaen)oates with x being an integer in the range of from 4 to 20, sugar esters, fatty acid esters, ascorbyl palmitate and mixtures thereof.

23. The formulation according to claim 21, wherein the emulsifier is selected from the group consisting of polyoxyethylene(20) sorbitan mono-laurate, polyoxyethylene(4) sorbitan mono-laurate, polyoxyethylene(20) sorbitan mono-palmitate, polyoxyethylene(20) sorbitan mono-stearate, polyoxyethylene(4) sorbitan mono-stearate, polyoxyethylene(20) sorbitan tri-stearate, polyoxyethylene(20) sorbitan mono-oleate, polyoxyethylene(5) sorbitan mono-oleate, polyoxyethylene(20) sorbitan tri-oleate and mixtures thereof.

24. The formulation according to claim 21, wherein the emulsifier is polyoxyethylene(20) sorbitan monostearate.

25. The formulation according to claim 3, wherein the formulation has a residua moisture content in the range of from 2.4 to 4.5 weight-%.

26. The formulation according to claim 4, wherein the formulation shows an extrusion loss of said lipophilic health ingredient of ≤12.5 weight-%, based on the total weight of the lipophilic health ingredient in the formulation, when pressed to tablets.

27. The formulation according to claim 4, wherein the formulation shows an extrusion loss of said lipophilic health ingredient of ≤10 weight-%, based on the total weight of the lipophilic health ingredient in the formulation, when pressed to tablets.

28. The formulation according to claim 1, wherein the formulation further contains an antioxidant suitable for food.

29. The formulation according to claim 9, wherein the emulsifier is selected from the group consisting of polyoxyethylen(x) sorbitan mono-$C_{10}$-$C_{20}$-alkan(dien/trien/pentaen)oates with x being 4, 5 or 20, polyoxyethylene(x) sorbitan tri-$C_{10}$-$C_{20}$-alkan(dien/trien/pentaen)oates with x being an integer in the range of from 4 to 20, sugar esters, fatty acid esters, ascorbyl palmitate and mixtures thereof.

30. The formulation according to claim 9, wherein the emulsifier is selected from the group consisting of polyoxyethylen(x) sorbitan mono-$C_{10}$-$C_{20}$-alkan(dien/trien/pentaen)oates with x being an integer in the range of from 4 to 20, polyoxyethylene(x) sorbitan tri-$C_{10}$-$C_{20}$-alkan(dien/trien/pentaen)oates with x being 4, 5 or 20, sugar esters, fatty acid esters, ascorbyl palmitate and mixtures thereof.

* * * * *

UNITED STATES PATENT AND TRADEMARK OFFICE
CERTIFICATE OF CORRECTION

PATENT NO. : 8,597,642 B2 Page 1 of 1
APPLICATION NO. : 12/669057
DATED : December 3, 2013
INVENTOR(S) : Diguet et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 792 days.

Signed and Sealed this
Twenty-second Day of September, 2015

Michelle K. Lee
*Director of the United States Patent and Trademark Office*